(12) United States Patent
Mang et al.

(10) Patent No.: US 7,790,767 B2
(45) Date of Patent: Sep. 7, 2010

(54) PLEUROMUTILIN DERIVATIVES CONTAINING A HYDROXYAMINO- OR ACYLOXYAMINOCYCLOALKYL GROUP

(75) Inventors: Rosemarie Mang, Vienna (AT); Gerd Ascher, Kundl/Tirol (AT); Mathias Ferencic, Vienna (AT); Werner Heilmayer, Zillingtal (AT); Rodger Novak, Vienna (AT)

(73) Assignee: Nabriva Therapeutics Forschungs GmbH, Vienna (AT)

( * ) Notice: Subject to any disclaimer, the term of this patent is extended or adjusted under 35 U.S.C. 154(b) by 503 days.

(21) Appl. No.: 11/814,672

(22) PCT Filed: Jun. 26, 2006

(86) PCT No.: PCT/AT2006/000260

§ 371 (c)(1),
(2), (4) Date: Nov. 15, 2007

(87) PCT Pub. No.: WO2007/000004

PCT Pub. Date: Jan. 4, 2007

(65) Prior Publication Data

US 2009/0306203 A1    Dec. 10, 2009

(30) Foreign Application Priority Data

Jun. 27, 2005 (GB) ................... 0513060.4
Aug. 3, 2005 (GB) ................... 0515997.5

(51) Int. Cl.
*A61K 31/215* (2006.01)
*C07C 69/74* (2006.01)

(52) U.S. Cl. ................ 514/530; 560/121; 560/125
(58) Field of Classification Search ............... None
See application file for complete search history.

(56) References Cited

FOREIGN PATENT DOCUMENTS

WO    WO 03/082260 A2    10/2003

OTHER PUBLICATIONS

International Search Report from PCT/AT2006/000260 dated Aug. 24, 2006.
Written Opinion of the International Searching Authority from PCT/AT2006/000260 dated Aug. 24, 2006.

*Primary Examiner*—Paul A Zucker
(74) *Attorney, Agent, or Firm*—Knobbs Martens Olson & Bear LLP

(57) ABSTRACT

The present invention relates to Compounds of general formula (I), wherein R is hydrogen and $R_1$ is hydroxy or acyloxy, or R is acyl and $R_1$ is hydroxy or acyloxy, X is sulphur, oxygen or $NR_{10}$, wherein $R_{10}$ is hydrogen or $(C_{1-4})$alkyl; Y is sulphur or oxygen; $R_2$ is hydrogen or one or more substituents, e.g. including substituents such as conventional in organic, e.g. (pleuro)mutilin, chemistry; $R_4$ is hydrogen or $(C_{1-4})$alkyl; $R_5$ is hydrogen or $(C_{1-4})$alkyl; $R_3$ and $R_3'$ are hydrogen, deuterium, or halogen; $R_6$, $R_7$ and $R_8$ are hydrogen, halogen or deuterium; m is a number selected from 0 to 4, n is a number selected from 0 to 10, and p is a number selected from 0 to 10; with the proviso that n plus p are at least 1. These Compounds are useful as pharmaceuticals, particularly as antimicrobials.

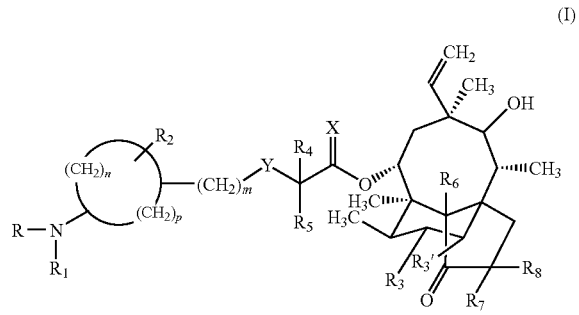

10 Claims, No Drawings

PLEUROMUTILIN DERIVATIVES CONTAINING A HYDROXYAMINO- OR ACYLOXYAMINOCYCLOALKYL GROUP

CROSS REFERENCE TO RELATED APPLICATIONS

This application claims to benefit and priority to and is a U.S. National Phase of PCT International Application Number PCT/AT2006/000260, filed on Jun. 26, 2006, designating the United States of America, which claims priority under U.S.C. §119 to European Applications 0513060.4 filed on Jun. 27, 2005 and 0515997.5 filed on Aug. 3, 2005. The disclosures of the above-referenced applications are hereby incorporated by this reference in their entirety.

The present invention relates to organic compounds, in particular pleuromutilins.

Pleuromutilin, a compound of formula A is a naturally occurring antibiotic, e.g. produced by the basidomycetes *Pleurotus mutilus* and *P. passeckerianus*, see e.g. The Merck Index, 12th edition, item 7694.

A number of further pleuromutilins having the principle ring structure of pleuromutilin and being substituted at the hydroxy group have been developed, e.g. as antimicrobials.

We have now found pleuromutilins with interesting activity.

A pleuromutilin provided by the present invention includes a pleuromutilin having the basic structural elements of the mutilin ring system as set out in formula PLEU wherein $R_{PLEU'}$ is vinyl or ethyl and the dotted line is a bond or is no bond.

The following numbering system is used in the present application:

The dotted line between positions 19 an 20 (and between positions 1 and 2) is a bond or is no bond. In a compound of formula A or of formula PLEU a hydrogen atom in positions 4, 7 and/or 8 of the ring system may be replaced by deuterium, and if the dotted line between positions 1 and 2 is no bond (single bond between positions 1 and 2) the ring system may be further substituted in positions 1 and/or 2, e.g. by halogen, deuterium or hydroxy. The group —O— in position 14 is further substituted, preferably by a substituted carbonyl group.

In one aspect the present invention provides a compound of general formula I

I wherein

R is hydrogen and $R_1$ is hydroxy or acyloxy, or

R is acyl and $R_1$ is hydroxy or acyloxy,

X is sulphur, oxygen or $NR_{10}$, wherein $R_{10}$ is hydrogen or $(C_{1-4})$alkyl;

Y is sulphur or oxygen;

$R_2$ is hydrogen or one or more substituents, e.g. including substituents such as conventional in organic, e.g. (pleuro) mutilin, chemistry;

$R_4$ is hydrogen or $(C_{1-4})$alkyl;

$R_5$ is hydrogen or $(C_{1-4})$alkyl;

$R_3$ and $R_3'$ are hydrogen, deuterium, or halogen;

$R_6$, $R_7$ and $R_8$ are hydrogen, halogen or deuterium;

m is a number selected from 0 to 4, n is a number selected from 0 to 10, and p is a number selected from 0 to 10;

with the proviso that n plus p are at least 1.

$R_2$ may include substituents such as halogen and $(C_{1-8})$ alkyl.

According to a preferred embodiment, $R_2$, $R_3$, $R_3'$, $R_4$, $R_5$, $R_6$ and $R_7$ are hydrogen, X is oxygen, Y is sulphur, m is a number selected from 0 to 4, preferably m is 0, n is a number selected from 0 to 8, preferably from 0 to 7, p is a number selected from 0 to 8, preferably from 0 to 7, with the proviso that n plus p are at least 2, preferably less than 9, and more preferably n plus p is 3 or 4;

e.g. wherein each single substituent defined may be a preferred substituent, independently from the other substituents defined.

Preferred compounds according to the invention are selected from the group consisting of 14-O-[((Hydroxy or acyloxy-amino)-cycloalkylsulfanyl- or -cycloalkyl-oxy)-acetyl, -thioacetyl or -imino-oxy]-mutilins, 14-O-[((Acyl-hydroxy or acyl-acyloxy-amino)-cycloalkylsulfanyl- or -cycloalkyl-oxy)-acetyl, -thioacetyl or -imino-oxy]-mutilins, 14-O-[((Hydroxy or acyloxy-amino-cycloalkyl)-alkylsulfanyl- or alkyl-oxy)-acetyl, -thioacetyl or -imino-oxy]-mutilins, 14-O-[(((Acyl-hydroxy or acyl-acyloxy-amino)-cycloalkyl)-alkylsulfanyl- or alkyl-oxy)-acetyl, -thioacetyl or -imino-oxy]-mutilins, 14-O-[((Hydroxy or acyloxy-amino-cycloalkyloxy)-alkylsulfanyl or alkyl-oxy)-acetyl, -thioacetyl or -imino-oxy]-mutilins, and 14-O-[(((Acyl-hydroxy or acyl-acyloxy-amino)-cycloalkyloxy)-alkylsulfanyl or alkyl-oxy)-acetyl, -thioacetyl or -imino-oxy]-mutilins.

Preferably, the compounds according to the present invention are selected from the group consisting of [(Hydroxy or acyloxy-amino)-cycloalkylsulfanyl]acetic acid mutilin-14-yl ester and [(Acyl-hydroxy or acyl-acyloxy-amino)-cycloalkylsulfanyl]-acetic acid mutilin-14-yl ester.

Particularly preferred compounds of the present invention are selected from the group consisting of

[3-(Hydroxyamino)-cyclopentylsulfanyl]acetic acid mutilin-14-yl ester,

[3-(Hydroxyamino)-cyclohexylsulfanyl]acetic acid mutilin-14-yl ester,

[3-(Formyl-hydroxy-amino)-cyclopentylsulfanyl]acetic acid mutilin-14-yl ester,

[3-(Formyl-hydroxy-amino)-cyclohexylsulfanyl]acetic acid mutilin-14-yl ester,

[3-(Acetyl-acetoxy-amino)-cyclohexylsulfanyl]acetic acid mutilin-14-yl ester,

[3-(Acetoxyamino)-cyclohexylsulfanyl]acetic acid mutilin-14-yl ester,

[3-(Isobutyryloxyamino)-cyclohexylsulfanyl]acetic acid mutilin-14-yl ester, and

[3-(Pivaloyloxyamino)-cyclohexylsulfanyl]acetic acid mutilin-14-yl ester,

In another aspect the present invention provides a compound of formula $I_p$

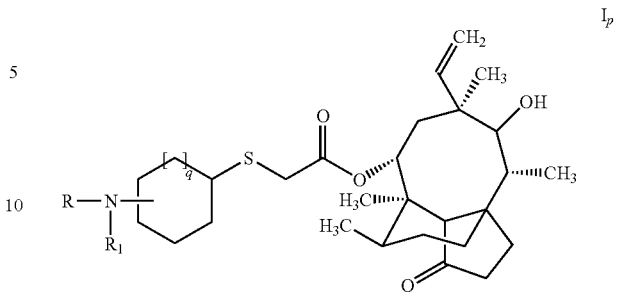

such as a compound of formula $I_{pp}$

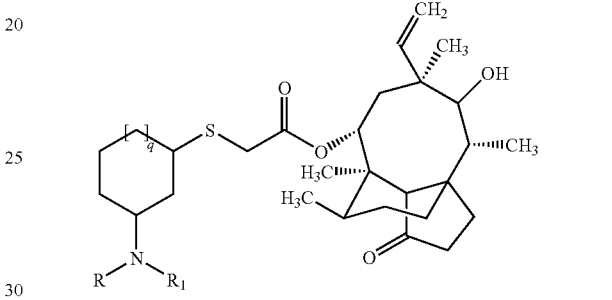

wherein R and $R_1$ are as defined above, and q is a number selected from 0 or 1.

In formula $I_p$ a group —N($RR_1$) may be in any position of the cycloalkyl ring system and is preferably in position 3 or in position 4.

A compound provided by the present invention is herein also designated as "compound(s) of (according to) the present invention". A compound of the present invention includes mutilin-14-yl acid esters as explicitly defined above and a compound of formula I, $I_p$ and $I_{pp}$. A compound of the present invention includes a compound in any form, e.g. in free form, in the form of a salt, in the form of a solvate and in the form of a salt and a solvate.

According to another aspect, the present invention provides a compound of the present invention in the form of a salt and/or solvate.

The salts include preferably pharmaceutically acceptable salts, although pharmaceutically unacceptable salts are included, e.g. for preparation/isolation/purification purposes.

A salt of a compound of the present invention includes a base salt or an acid addition salt. Pharmaceutically acceptable base salts include ammonium salts such as trimethylammonium salt, alkali metal salts such as those of sodium and potassium, alkaline earth metal salts such as those of calcium and magnesium, and salts with organic bases, including salts of primary, secondary and tertiary amines, such as isopropylamine, diethylamine, ethanolamine, trimethylamine, dicyclohexyl amine and N-methyl-D-glucamine, preferably sodium salts. Acid addition salts include salts of a compound of the present invention with an acid, e.g. hydrogen fumaric acid, fumaric acid, tartaric acid, ethane-1,2-disulphonic acid, maleic acid, naphthalin-1,5-sulphonic acid, hydrochloric acid, deuterochloric acid, preferably hydrochloric acid.

A compound of the present invention in free form may be converted into a corresponding compound in the form of a salt, and vice versa. A compound of the present invention in free form or in the form of a salt and/or in the form of a solvate may be converted into a corresponding compound in free form or in the form of a salt in non-solvated form, and vice versa.

A compound of the present invention may exist in the form of isomers and mixtures thereof, e.g. optical isomers, diastereoisomers, cis/trans conformers. A compound of the present invention may e.g. contain asymmetric carbon atoms and may thus exist in the form of enantiomers or diastereoisomers and mixtures thereof, e.g. racemates. Any asymmetric carbon atom may be present in the (R)-, (S)- or (R,S)-configuration, preferably in the (R)- or (S)-configuration.

For example, in a compound of formula $I_{pp}$ the carbon atom of the cycloalkyl ring which is attached to the side sulphur atom, and the carbon atom of the cycloalkyl ring to which the group —N(RR$_1$) is attached, are both asymmetric carbon atoms. Substituents attached to such asymmetric carbon atom may thus exist in (R) and (S) configuration. The configuration of substituents attached to asymmetric carbon atoms of the mutilin-ring is preferably the same as in natural pleuromutilin.

Isomeric mixtures may be separated as appropriate, e.g. according, e.g. analogously, to a method as conventional, to obtain pure isomers. The present invention includes a compound of the present invention in any isomeric form and in any isomeric mixture. The present invention also includes tautomers of a compound of the present invention, where tautomers can exist.

Any compound described herein, e.g. a compound of the present invention and intermediates in their production may be prepared as appropriate, e.g. according, e.g. analogously, to a method as conventional, e.g., or as specified herein.

In another aspect the present invention provides a process for the preparation of a compound of formula I, comprising the following steps a. reacting a compound of formula II

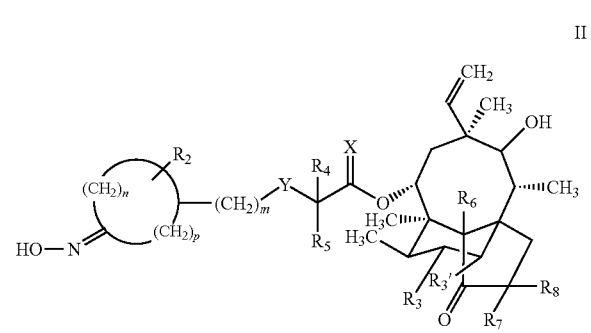

wherein X, Y, R$_2$, R$_3$, R'$_3$, R$_4$, R$_5$, R$_6$, n and p are as defined above, in acetic acid with sodium cyanoborohydride and isolating a compound of formula I, wherein R is hydrogen and R$_1$ is hydroxy, and X, Y, R$_2$, R$_3$, R'$_3$, R$_4$, R$_5$, R$_6$, n and p are as defined above, and, optionally b. reacting a compound of formula I, wherein R is hydrogen and R$_1$ is hydroxy, and X, Y, R$_2$, R$_3$, R'$_3$, R$_4$, R$_5$, R$_6$, n and p are as defined above, with an acylating agent such as carboxylic acid anhydride, carboxylic acid halogen or a preheated mixture of carboxylic acid in acetic anhydride, and isolating a compound of formula I wherein R is hydrogen or acyl and R$_1$ is hydroxy or acyloxy and X, Y, R$_2$, R$_3$, R'$_3$, R$_4$, R$_5$, R$_6$, n and p are as defined above, from the reaction mixture.

A compound of formula II may be e.g. obtained according, e.g. analogously, as disclosed in WO0382260.

In another aspect the present invention provides a process for the preparation of 14-O-[((Hydroxyamino)-cycloalkylsulfanyl- or -cycloalkyl-oxy)-acetyl, -thioacetyl or -imino-oxy]-mutilins, 14-O-[((Hydroxyamino-cycloalkyl)-alkylsulfanyl- or alkyl-oxy)-acetyl, -thioacetyl or -imino-oxy]-mutilins, or 14-O-[((Hydroxyamino-cycloalkyloxy)-alkylsulfanyl or alkyl-oxy)-acetyl, -thioacetyl or -imino-oxy]-mutilins, respectively, comprising reacting 14-O-[((Hydroxyimino)-cycloalkylsulfanyl- or -cycloalkyl-oxy)-acetyl, -thioacetyl or -imino-oxy]-mutilins, 14-O-[((Hydroxyimino-cycloalkyl)-alkylsulfanyl- or alkyl-oxy)-acetyl, -thioacetyl or -imino-oxy]-mutilins, or 14-O-[((Hydroxyimino-cycloalkyloxy)-alkylsulfanyl or alkyl-oxy)-acetyl, -thioacetyl or -imino-oxy]-mutilins, respectively, in acetic acid with sodium cyanoborohydride and isolating 14-O-[((Hydroxyamino)-cycloalkylsulfanyl- or -cycloalkyl-oxy)-acetyl, -thioacetyl or -imino-oxy]-mutilins, 14-O-[((Hydroxyamino-cycloalkyl)-alkylsulfanyl- or alkyl-oxy)-acetyl, -thioacetyl or -imino-oxy]-mutilins, or 14-O-[((Hydroxyamino-cycloalkyloxy)-alkylsulfanyl or alkyl-oxy)-acetyl, -thioacetyl or -imino-oxy]-mutilins, respectively, from the reaction mixture.

In another aspect the present invention provides a process for the preparation of 14-O-[((Acyloxyamino)-cycloalkylsulfanyl- or -cycloalkyl-oxy)-acetyl, -thioacetyl or -imino-oxy]-mutilins, 14-O-[((Acyl-hydroxy or acyl-acyloxy-amino)-cycloalkylsulfanyl- or -cycloalkyl-oxy)-acetyl, -thioacetyl or -imino-oxy]-mutilins, 14-O-[((Acyloxyamino-cycloalkyl)-alkylsulfanyl- or alkyl-oxy)-acetyl, -thioacetyl or -imino-oxy]-mutilins, 14-O-[(((Acyl-hydroxy or acyl-acyloxy-amino)-cycloalkyl)-alkylsulfanyl- or alkyl-oxy)-acetyl, -thioacetyl or -imino-oxy]-mutilins, 14-O-[((Acyloxyamino-cycloalkyloxy)-alkylsulfanyl or alkyl-oxy)-acetyl, -thioacetyl or -imino-oxy]-mutilins, or 14-O-[(((Acyl-hydroxy or acyl-acyloxy-amino)-cycloalkyloxy)-alkylsulfanyl or alkyl-oxy)-acetyl, -thioacetyl or -imino-oxy]-mutilins, respectively, comprising reacting 14-O-[((Hydroxyamino)-cycloalkylsulfanyl- or -cycloalkyl-oxy)-acetyl, -thioacetyl or -imino-oxy]-mutilins, 14-O-[((Hydroxyamino-cycloalkyl)-alkylsulfanyl- or alkyl-oxy)-acetyl, -thioacetyl or -imino-oxy]-mutilins, or 14-O-[((Hydroxyamino-cycloalkyloxy)-alkylsulfanyl or alkyl-oxy)-acetyl, -thioacetyl or -imino-oxy]-mutilins, respectively, with an acylating agent such as carboxylic acid anhydride, carboxylic acid halogen or a preheated mixture of carboxylic acid in acetic anhydride and isolating 14-O-[((Acyloxyamino)-cycloalkylsulfanyl- or -cycloalkyl-oxy)-acetyl, -thioacetyl or -imino-oxy]-mutilins, 14-O-[((Acyl-hydroxy or acyl-acyloxy-amino)-cycloalkylsulfanyl- or -cycloalkyl-oxy)-acetyl, -thioacetyl or -imino-oxy]-mutilins, 14-O-[((Acyloxyamino-cycloalkyl)-alkylsulfanyl- or alkyl-oxy)-acetyl, -thioacetyl or -imino-oxy]-mutilins, 14-O-[(((Acyl-hydroxy or acyl-acyloxy-amino)-cycloalkyl)-alkylsulfanyl- or alkyl-oxy)-acetyl, -thioacetyl or -imino-oxy]-mutilins, 14-O-[((Acyloxyamino-cycloalkyloxy)-alkylsulfanyl or alkyl-oxy)-acetyl, -thioacetyl or -imino-oxy]-mutilins, or 14-O-[(((Acyl-hydroxy or acyl-acyloxy-amino)-cycloalkyloxy)-alkylsulfanyl or alkyl-oxy)-acetyl, -thioacetyl or -imino-oxy]-mutilins, respectively, from the reaction mixture.

A compound obtained by a process provided by the present invention may be converted into a corresponding salt, according, e.g. analogously, to a method as conventional, e.g. by treatment with an acid or a base such as a metal base or an organic base, respectively, to obtain an acid addition salt or a base addition salt, respectively, and vice versa. A compound obtained by a process provided by the present invention in the form of a salt may be converted into the corresponding compound in the form of a free base, according, e.g. analogously, to a method as conventional, e.g. by treatment with an acid if a base addition salt is obtained and by treating with a base, e.g. a metal hydroxide if an acid addition salt is obtained.

The compounds of the present invention exhibit pharmacological activity and are therefore useful as pharmaceuticals.

For example, the compounds of the present invention show antimicrobial, e.g. antibacterial, activity against gram positive bacteria, such as coagulase positive Staphylococci, e.g. *Staphylococcus aureus*, coagulase negative Staphylococci, e.g. *Staphylococcus epidermidis, Staphylococcus haemolyticus*, and Streptococci, e.g. *Streptococcus pyogenes, Streptococcus pneumoniae, Enterococci*, e.g. *Enterococcus faecium* and *Listeria monocytogenes* and against gram negative bacteria such as *Moraxella*, e.g. *Moraxella catarrhalis*, and *Haemophilus*, e.g. *Haemophilus influenzae*, and *Legionella*, e.g. *Legionella pneumophila, Neisseriaceae*, e.g. *Neisseria gonorrhoeae*, as well as against Mycoplasms, *Chlamydia* and obligatory anaerobes, e.g. *Bacteroides fragilis, Clostridium difficile, Fusobacterium* spp., and *Propionibacterium* spp.

The in vitro activity against aerobic bacteria was determined by Agar Dilution Test or Microdilution Test according to the Clinical and Laboratory Standards Institute (CLSI, former NCCLS) Document M7-A7 Vol. 26, No. 2: "Methods for dilution Antimicrobial Susceptibility Tests for Bacteria that Grow Aerobically—Approved Standard; Seventh Edition (2006)"; and the test against anaerobic bacteria was performed according to the Clinical and Laboratory Standards Institute (CLSI, former NCCLS), Document, M11-A6, Vol. 24, No. 2: "Methods for Antimicrobial Susceptibility Testing of Anaerobic Bacteria-Approved Standard; Sixth Edition (2004)" and the in vivo activity was tested by the septicaemia mouse model against *Staphylococcus aureus*.

Compounds of the present invention are therefore suitable for the treatment and prevention of diseases which are mediated by microbes, e.g. by bacteria. Diseases which may also be treated include e.g. diseases mediated by *Helicobacter*, such as *Helicobacter pylori*, and diseases mediated by *Mycobacterium tuberculosis*. Diseases which may also be treated include in general inflammatory diseases, where microbes are mediating said inflammation, e.g. including acne.

In another aspect the present invention provides a compound of the present invention for use as a pharmaceutical, preferably as an antimicrobial, such as an antibiotic, e.g. and an anti-anaerobic.

In another aspect the present invention provides a compound of the present invention for use in acne treatment.

In a further aspect the present invention provides a compound of the present invention for use in the preparation of a medicament for the treatment of diseases, mediated by microbes, such as bacterials, for example diseases mediated by bacteria, e.g. selected from Staphylococci, Streptococci, Enterococci;

diseases mediated by bacteria, e.g. selected from *Moraxella, Haemophilus, Legionella, Neisseriaceae*;

diseases mediated by *Helicobacter*;

diseases mediated by *Mycobacterium tuberculosis*;

e.g. diseases mediated by Mycoplasms, *Chlamydia* and obligatory anaerobes; and for the treatment of acne.

In a further aspect the present invention provides a method of treatment of diseases mediated by microbes which comprises administering to a subject in need of such treatment an effective amount of a compound of the present invention e.g. in the form of a pharmaceutical composition.

In a further aspect the present invention provides a method of treatment of acne which comprises administering to a subject in need of such treatment an effective amount of a compound of the present invention e.g. in the form of a pharmaceutical composition.

Treatment includes treatment and prophylaxis.

For antimicrobial and acne treatment, the appropriate dosage will, of course, vary depending upon, for example, the chemical nature and the pharmacokinetic data of a compound of the present invention employed, the individual host, the mode of administration and the nature and severity of the conditions being treated. However, in general, for satisfactory results in larger mammals, for example humans, an indicated daily dosage is in the range from about 0.5 mg to 3 g of a compound of the present invention conveniently administered, for example, in divided doses up to four times a day.

A compound of the present invention may be administered by any conventional route, for example enterally, e.g. including nasal, buccal, rectal, oral administration; parenterally, e.g. including intravenous, intramuscular, subcutaneous administration; or topically, e.g. including epicutaneous, intranasal, intratracheal administration, e.g. in form of coated or uncoated tablets, capsules, injectable solutions or suspensions, e.g. in the form of ampoules, vials, in the form of creams, gels, pastes, inhaler powder, foams, tinctures, lip sticks, drops, sprays, or in the form of suppositories, e.g. in analogous manner to macrolides, such as erythromycins, e.g. clarithromycin or azithromycin.

A compound of the present invention may be administered in the form of a pharmaceutically acceptable salt, e.g. an acid addition salt or a base addition salt, e.g. a metal salt, or in free form, optionally in the form of a solvate. A compound of the present invention in the form of a salt exhibits the same order of activity as the compound in free form, optionally in the form of a solvate.

A compound of the present invention may be used for pharmaceutical treatment according to the present invention alone or in combination with one or more other pharmaceutically active agents. Such other pharmaceutically active agents include e.g. other antibiotics and antiinflammatory agents, and, if a compound of the present invention is used in the treatment of acne, other pharmaceutically agents include furthermore agents which are active against acne.

Combinations include fixed combinations, in which two or more pharmaceutically active agents are in the same formulation; kits, in which two or more pharmaceutically active agents in separate formulations are sold in the same package, e.g. with instruction for co-administration; and free combinations in which the pharmaceutically active agents are packaged separately, but instruction for simultaneous or sequential administration are given.

In another aspect the present invention provides a pharmaceutical composition comprising a compound of the present invention in free form or in the form of a pharmaceutically acceptable salt and/or in the form of a solvate in association with at least one pharmaceutical, excipient, e.g. carrier or diluent, e.g. including fillers, binders, disintegrators, flow conditioners, lubricants, sugars and sweeteners, fragrances, preservatives, stabilizers, wetting agents and/or emulsifiers, solubilizers, salts for regulating osmotic pressure and/or buffers.

In another aspect the present invention provides a pharmaceutical composition according to the present invention, further comprising another pharmaceutically active agent.

Such pharmaceutical compositions may be manufactured according, e.g. analogously, to a method as conventional, e.g. by mixing, granulating, coating, dissolving or lyophilizing processes. Unit dosage form may contain, for example, from about 0.5 mg to about 1000 mg, such as 1 mg to about 100 mg.

The compounds of the present invention are additionally suitable as veterinary agents, e.g. veterinary active compounds, e.g. in the prophylaxis and in the treatment of microbial, e.g. bacterial diseases, in animals, such as fowl, pigs and calves, e.g., and for diluting fluids for artificial insemination and for egg-dipping techniques.

In another aspect the present invention provides a compound of the present invention for use as a veterinary agent.

In a further aspect the present invention provides a compound of the present invention for the preparation of a veterinary composition which is useful as a veterinary agent.

In another aspect the present invention provides a veterinary method for the prophylaxis and the treatment of microbial, e.g. bacterial diseases which comprises administering to a subject in need of such treatment an effective amount of a compound of the present invention, e.g. in the form of a veterinary composition.

For use of the active compounds of the present invention as a veterinary agent, the dosage will of course vary depending upon the size and age of the animal and the effect desired; for example for prophylactic treatment relatively low doses would be administered over a longer time period, e.g. 1 to 3 weeks. Preferred doses in drinking water are from 0.0125 to 0.05 weight by volume, particularly 0.0125 to 0.025; and in foodstuffs from 20 to 400 g/metric ton, preferably 20 to 200 g/metric ton. It is preferred to administer the active compounds of the present invention as a veterinary agent to hens in drinking water, to pigs in foodstuff and to calves orally or parenterally, e.g. in the form of oral or parenteral preparations.

In the following examples all temperatures are in degrees Celsius (° C.) and are uncorrected. The compounds 14-O-{[3-(hydroxyimino)-cyclohexylsulfanyl]-acetyl}-mutilin and 14-O-{[3-(hydroxyimino)-cyclopentylsulfanyl]-acetyl}-mutilin used as a starting material may be e.g. obtained as disclosed in WO0382260.

EXAMPLE 1

Step A. Mixtures of Cis and Trans Diastereomers

14-O-{[(1S,3S)-3-Hydroxylamino-cyclohexylsulfanyl]-acetyl}-mutilin (a)
14-O{[(1R,3R)-3-Hydroxylamino-cyclohexylsulfanyl]-acetyl}-mutilin (b)
14-O-{[(1S,3R)-3-Hydroxylamino-cyclohexylsulfanyl]-acetyl}-mutilin (c)
14-O-{[(1R,3S)-3-Hydroxylamino-cyclohexylsulfanyl]-acetyl}-mutilin (d)

537 mg of sodium cyanoborohydride are added to a solution of 4.32 g of 14-O-{[3-(hydroxyimino)-cyclohexylsulfanyl]-acetyl}-mutilin in acetic acid and the mixture obtained is stirred for 16 hours at room temperature. From the mixture obtained solvent is evaporated (nearly to dryness) and the evaporation residue is taken up in saturated sodium hydrogen carbonate and extracted three times with ethyl acetate. The organic phase obtained is dried, solvent is evaporated and the evaporation residue is subjected to chromatography (cyclohexane/ethyl acetate=1:20+0.5% aqueous ammonium hydroxide).

1.17 g of a mixture of trans diastereomers (a) and (b) and 0.62 g of a mixture of cis diastereomers (c) and (d) are obtained.

Mixture of Trans Diastereomers (A) and (B):
$^1$H NMR: (DMSO-$d_6$): 7.00 (s, 1H, NH), 6.13 (dd, 1H, Hash J=17.7 Hz, J=11.2 Hz), 5.54 (d, 1H, $H_{14}$, J=8.3 Hz), 5.42 (bs, 1H, NHO$\underline{H}$), 5.07 (dd, 1H, $H_{20cis}$, J=17.7 Hz, J=1.7 Hz), 5.03 (dd, 1H, $H_{20trans}$, J=11.2 Hz, J=1.7 Hz), 4.50, 4.49 (2d, 1H, 11-OH, J=6.1 Hz), 3.42 (t, 1H, $H_{11}$, J=6.1 Hz), 2.80-3.30 (m, 4H, $H_{22}$, $H_{1'}$, $H_{3'}$), 2.4 (s, 1H, H4), 1.35 (s, 3H, $(CH_3)_{15}$), 1.05 (s, 3H, $(CH_3)_{18}$), 0.81 (d, 3H, $(CH_3)_{17}$, J=7.0 Hz), 0.63 (d, 3H, $(CH_3)_{16}$, J=6.8 Hz).

Mixture of Cis Diastereomers (C) and (D):
$^1$H NMR: (DMSO-$d_6$): 7.02 (s, 1H, NH), 6.14 (dd, 1H, $H_{19}$, J=17.7 Hz, J=11.1 Hz), 5.56 (d, 1H, $H_{14}$, J=8.2 Hz), 5.48 (bs, 1H, NHO$\underline{H}$), 5.07 (dd, 1H, $H_{20cis}$, J=17.7 Hz, J=1.7 Hz), 5.03 (dd, 1H, $H_{20trans}$, J=11.1 Hz, J=1.7 Hz), 4.49 (d, 1H, 11-OH, J=6.1 Hz), 3.42 (t, 1H, $H_{11}$, J=6.1 Hz), 3.23 (m, 1H, $H_{22}$), 2.68, 2.56 (2m, 2H, $H_{1'}$, $H_{3'}$), 2.4 (s, 1H, H4), 1.35 (s, 3H, $(CH_3)_{15}$), 1.05 (s, 3H, $(CH_3)_{18}$), 0.81 (d, 3H, $(CH_3)_{17}$, J=7.0 Hz), 0.63 (d, 3H, $(CH_3)_{16}$, J=6.7 Hz).

Step B. Mixture of Trans Diastereomers

14-O-{[(1S,3S)-3-Hydroxylamino-cyclohexylsulfanyl]-acetyl}-mutilin in the form of a hydrochloride and 14-O-{[(1R,3R)-3-Hydroxylamino-cyclohexylsulfanyl]-acetyl}-mutilin in the form of a hydrochloride 150 mg of a mixture of trans diastereomers 14-O-{[(1S,3S)-3-hydroxyamino-cyclohexylsulfanyl]-acetyl}-mutilin and 14-O-{[(1R,3R)-3-hydroxyamino-cyclohexylsulfanyl]-acetyl}-mutilin are distributed between diethyl ether and 0.1 N HCl and the aqueous layer obtained is subjected to lyophilization.

134 mg of a mixture of trans diastereomers 14-O-{[(1S,3S)-3-hydroxyamino-cyclohexylsulfanyl]-acetyl}-mutilin in the form of a hydrochloride and 14-O-{[(1R,3R)-3-hydroxyamino-cyclohexylsulfanyl]-acetyl}-mutilin in the form of a hydrochloride are obtained.

$^1$H NMR: (DMSO-$d_6$): 11.20 (s, 2H, $NH_2^+$), 10.60 (s, 1H, $NH_2^+$OH), 6.13 (dd, 1H, $H_{19}$, J=17.7 Hz, J=11.2 Hz), 5.55 (d, 1H, $H_{14}$, J=8.3 Hz), 5.06 (dd, 1H, $H_{20cis}$, J=17.7 Hz, J=1.8 Hz), 5.03 (dd, 1H, $H_{20trans}$, J=11.2 Hz, J=1.8 Hz), 4.52 (m, 1H, 11-OH), 3.15-3.45 (m, 5H, $H_{11}$, $H_{22}$, $H_{1'}$, $H_{3'}$), 2.4 (s, 1H, H4), 1.35 (s, 3H, $(CH_3)_{15}$), 1.05 (s, 3H, $(CH_3)_{18}$), 0.81 (d, 3H, $(CH_3)_{17}$, J=7.0 Hz), 0.63 (d, 3H, $(CH_3)_{16}$, J=6.8 Hz).

MS-ESI: 508 ($M^+$)

EXAMPLE 2

Mixture of Cis Diastereomers

14-O-{[(1S,3R)-3-Hydroxyamino-cyclohexylsulfanyl]-acetyl}-mutilin in the form of a hydrochloride and 14-O-{[(1R,3S)-3-Hydroxyamino-cyclohexylsulfanyl]-acetyl}-mutilin in the form of a hydrochloride are prepared from a mixture of cis diastereomers 14-O-{[(1S,3R)-3-hydroxyamino-cyclohexylsulfanyl]-acetyl}-mutilin and 14-O-{[(1R,3S)-3-hydroxyamino-cyclohexylsulfanyl]-acetyl}-mutilin of Example 1 Step A) analogously to the method of Example 1 Step B.

¹H NMR: (DMSO-d$_6$): 11.25 (s, 2H, NH$_2^+$), 10.70 (s, 1H, NH$_2^{+OH)}$, 6.14 (dd, 1H, H19, J=17.6 Hz, J=11.0 Hz), 5.55 (d, 1H, H$_{14}$, J=8.2 Hz), 5.06 (m, 2H, H$_{20cis}$, H$_{20trans}$), 4.52 (m, 1H, 11-OH), 2.70-3.50 (m, 5H, H$_{11}$, H$_{22}$, H$_{1'}$, H$_{3'}$), 2.4 (s, 1H, H4), 1.35 (s, 3H, (CH$_3$)$_{15}$), 1.05 (s, 3H, (CH$_3$)$_{18}$), 0.82 (d, 3H, (CH$_3$)$_{17}$, J=6.8 Hz), 0.63 (d, 3H, (CH$_3$)$_{16}$, J=6.9 Hz).

MS-ESI: 508 (M$^+$)

EXAMPLE 3

14-O-{[3-Hydroxyamino-cyclopentylsulfanyl]-acetyl}-mutilin in the form of a hydrochloride is prepared analogously to Example 1, but using 14-O-{[3-(hydroxyimino)-cyclopentylsulfanyl]-acetyl}-mutilin instead of 14-O-{[3-(hydroxyimino)-cyclohexylsulfanyl]-acetyl}-mutilin.

¹H NMR: (DMSO-d$_6$): 11.35 (s, 2H, NH$_2^+$), 10.85 (s, 1H, NH$_2^+$OH), 6.15 (dd, 1H, H19, J=17.7 Hz, J=11.2 Hz), 5.55 (d, 1H, H$_{14}$, J=8.3 Hz), 5.06 (dd, 1H, H$_{20cis}$, J=17.7 Hz, J=1.3 Hz), 5.02 (dd, 1H, H$_{20trans}$, J=11.2 Hz, J=1.3 Hz), 4.55 (bs, 1H, 11-OH), 3.80, 3.70 (2m, 1H, H$_{1'}$), 3.0-3.5 (m, 4H, H$_{11}$, H$_{22}$, H$_{3'}$), 2.4 (s, 1H, H4), 1.35 (s, 3H, (CH$_3$)$_{15}$), 1.05 (s, 3H, (CH$_3$)$_{18}$), 0.82 (d, 3H, (CH$_3$)$_{17}$, J=7.0 Hz), 0.63 (d, 3H, (CH$_3$)$_{16}$, J=6.8 Hz).

MS-ESI: 494 (M$^+$)

EXAMPLE 4

Step A. Mixtures of Trans Diastereomers

14-O-{[(1S,3S)-3-(Formyl-hydroxy-amino)-cyclohexylsulfanyl]-acetyl}-mutilin

14-O-1-{[(1R,3R)-3-(Formyl-hydroxy-amino)-cyclohexylsulfanyl]-acetyl}-mutilin 0.9 ml of formic acid in 1.9 ml of acetic anhydride are heated to 50° and the mixture obtained is cooled. To the mixture obtained 1.01 g of a mixture of trans diastereomers 14-O-{[(1S,3S)-3-hydroxyamino-cyclohexylsulfanyl]-acetyl}-mutilin and 14-O-{[(1R,3R)-3-hydroxyamino-cyclohexylsulfanyl]-acetyl}-mutilin (Example 1 Step A) are added at 0° and the mixture obtained is stirred 16 hours. From the mixture obtained solvent is evaporated (to dryness) and the evaporation residue is subjected to chromatography (cyclohexane/ethyl acetate=1:2+0.5% acetic acid).

221 mg of a mixture of trans diastereomers of 14-O-{[(1S,3S)-3-(formyl-hydroxy-amino)-cyclohexylsulfanyl]-acetyl}-mutilin and 14-O-{[(1R,3R)-3-(formyl-hydroxy-amino)-cyclohexylsulfanyl]-acetyl}-mutilin are obtained.

¹H NMR: (DMSO-d$_6$): 9.30 (bs, 1H, NOH), 8.18, 7.98 (2s, 1H, CHO), 6.13 (dd, 1H, H$_{19}$, J=17.7 Hz, J=11.1 Hz), 5.54 (d, 1H, H$_{14}$, J=8.3 Hz), 5.04 (m, 2H, H$_{20cis}$, H$_{20trans}$), 4.50 (bs, 1H, 11-OH), 4.29, 3.80 (2m, 1H, H$_{3'}$), 3.10-3.60 (m, 4H, H$_1$, H$_{22}$, H$_{1'}$), 2.4 (s, 1H, H4), 1.35 (s, 3H, (CH$_3$)$_{15}$), 1.05 (s, 3H, (CH$_3$)$_{18}$), 0.81 (d, 3H, (CH$_3$)$_{17}$, J=6.9 Hz), 0.63 (d, 3H, (CH$_3$)$_{16}$, J=7.0 Hz).

MS-ESI: 558 (MNa$^+$)

Step B. Mixtures of Trans Diastereomers

14-O-{[(1S,3S)-3-(Formyl-hydroxy-amino)-cyclohexylsulfanyl]-acetyl}-mutilin in the form of a sodium salt and 14-O-{[(1R,3R)-3-(Formyl-hydroxy-amino)-cyclohexylsulfanyl]-acetyl}-mutilin in the form of a sodium salt 142 mg of a mixture of trans diastereomers 14-O-{[(1S,3S)-3-(formyl-hydroxy-amino)-cyclohexylsulfanyl]-acetyl}-mutilin and 14-O-{[(1R,3R)-3-(formyl-hydroxy-amino)-cyclohexylsulfanyl]-acetyl}-mutilin are dissolved in 10 ml of dioxane and the mixture obtained is treated with 2.4 ml of 0.1 N NaOH. The mixture obtained is subjected to lyophilization.

A mixture of trans diastereomers 14-O-{[(1S,3S)-3-(formyl-hydroxy-amino)-cyclohexylsulfanyl]-acetyl}-mutilin sodium salt and 14-O-{[(1R,3R)-3-(formyl-hydroxy-amino)-cyclohexylsulfanyl]-acetyl}-mutilin in the form of a sodium salt is obtained.

¹H NMR: (DMSO-d$_6$): 7.99, 7.70 (2bs, 1H, CHO), 6.12 (dd, 1H, H$_{19}$, J=17.7 Hz, J=11.1 Hz), 5.54 (d, 1H, H$_{14}$, J=8.0 Hz), 4.94-5.18 (m, 2H, H$_{20cis}$, H$_{20trans}$), 4.50 (bs, 1H, 11-OH), 4.25 (m, 1H, H$_{3'}$), 3.00-3.60 (m, 4H, H$_{11}$, H$_{22}$, H$_{1'}$), 2.4 (s, 1H, H4), 1.35 (s, 3H, (CH$_3$)$_{15}$), 1.05 (s, 3H, (CH$_3$)$_{18}$), 0.81 (d, 3H, (CH$_3$)$_{17}$, J=6.5 Hz), 0.63 (d, 3H, (CH$_3$)$_{16}$, J=6.4 Hz).

MS-ESI: 534 (MN), 558 (MNa$^+$)

EXAMPLE 5

Mixtures of Cis Diastereomers

14-O-{[(1S,3R)-3-(Formyl-hydroxy-amino)-cyclohexylsulfanyl]-acetyl}-mutilin

14-O-{-[(1R,3S)-3-(Formyl-hydroxy-amino)-cyclohexylsulfanyl]-acetyl}-mutilin are prepared from a mixture of cis diastereomers 14-O-{[(1S,3R)-3-hydroxyamino-cyclohexylsulfanyl]-acetyl}-mutilin and 14-O-{[(1R,3S)-3-hydroxyamino-cyclohexylsulfanyl]-acetyl}-mutilin (Example 1 Step A) analogously to the method of Example 4, Step A.

¹H NMR: (DMSO-d$_6$): 9.40 (bs, 1H, NOH), 8.18, 7.94 (2s, 1H, CHO), 6.13 (dd, 1H, H$_{19}$, J=17.7 Hz, J=11.2 Hz), 5.54 (d, 1H, H$_{14}$, J=8.3 Hz), 5.06 (dd, 1H, H$_{20cis}$, J=17.7 Hz, J=1.7 Hz), 5.03 (dd, 1H, H$_{20trans}$, J=11.2 Hz, J=1.7 Hz), 4.49 (bs, 1H, 11-OH), 4.00 (m, 1H, H$_{3'}$), 3.10-3.60 (m, 3H, H$_{11}$, H$_{22}$), 2.76 (m, 1H, H$_{1'}$), 2.4 (s, 1H, H4), 1.35 (s, 3H, (CH$_3$)$_{15}$), 1.05 (s, 3H, (CH$_3$)$_{18}$), 0.81 (d, 3H, (CH$_3$)$_{17}$, J=7.0 Hz), 0.63 (d, 3H, (CH$_3$)$_{16}$, J=7.0 Hz).

MS-ESI: 558 (MNa$^+$)

Mixtures of cis Diastereomers:

14-O-{[(1S,3R)-3-(Formyl-hydroxy-amino)-cyclohexylsulfanyl]-acetyl}-mutilin in the form of a sodium salt and 14-O-{[(1R,3S)-3-(Formyl-hydroxy-amino)-cyclohexylsulfanyl]-acetyl}-mutilin in the form of a sodium salt are prepared from a mixture of cis diastereomers 14-O-{[(1S,3R)-3-(formyl-hydroxy-amino)-cyclohexylsulfanyl]-acetyl}-mutilin and 14-O-{[(1R,3S)-3-(formyl-hydroxy-amino)-cyclohexylsulfanyl]-acetyl}-mutilin analogously to the method of Example 4 Step B.

¹H NMR: (DMSO-d$_6$): 8.05, 7.75 (2bs, 1H, CHO), 6.13 (dd, 1H, H$_{19}$, J=17.7 Hz, J=11.2 Hz), 5.54 (d, 1H, H$_{14}$, J=8.2 Hz), 5.00-5.10 (m, 2H, H$_{20cis}$, H$_{20trans}$), 4.50 (bs, 1H, 11-OH), 3.97 (m, 1H, H$_{3'}$), 3.10-3.40 (m, 3H, H$_{11}$, H$_{22}$), 2.70 (m, 1H, H$_{1'}$), 2.4 (s, 1H, H4), 1.35 (s, 3H, (CH$_3$)$_{15}$), 1.05 (s, 3H, (CH$_3$)$_{18}$), 0.81 (d, 3H, (CH$_3$)$_{17}$, J=6.1 Hz), 0.63 (d, 3H, (CH$_3$)$_{16}$, J=6.6 Hz).

MS-ESI: 534 (M$^-$), 558 (MNa$^+$)

EXAMPLE 6

14-O-{[3-(Formyl-hydroxy-amino)-cyclopentylsulfanyl]-acetyl}-mutilin is prepared from 14-O-{[(3-hydroxyamino-cyclopentylsulfanyl]-acetyl}-mutilin (Example 3) analogously to the method of Example 4 Step A.

$^1$H NMR: (DMSO-$d_6$): 9.85, 9.43 (2bs, 1H, NOH), 8.18, 7.93 (2s, 1H, CHO), 6.14 (dd, 1H, $H_{19}$, J=17.7 Hz, J=11.2 Hz), 5.55 (d, 1H, $H_{14}$, J=8.2 Hz), 5.06 (dd, 1H, $H_{20cis}$, J=17.7 Hz, J=1.8 Hz), 5.03 (dd, 1H, $H_{20trans}$, J=11.2 Hz, J=1.8 Hz), 4.76, 4.61, 4.35, 4.23 (2bs, 1H, $H_{3'}$), 4.48 (d, 1H, 11-OH, J=6.1 Hz), 3.41 (t, 1H, $H_{11}$, J=6.1 Hz), 3.15-3.35 (m, 2H, $H_{22}$), 3.11 (m, 1H, $H_{1'}$), 2.4 (s, 1H, H4), 1.35 (s, 3H, $(CH_3)_{15}$), 1.05 (s, 3H, $(CH_3)_{18}$), 0.81 (d, 3H, $(CH_3)_{17}$, J=7.0 Hz), 0.63 (d, 3H, $(CH_3)_{16}$, J=6.8 Hz).

MS-ESI: 544 (MNa$^+$)

14-O-{[3-(Formyl-hydroxy-amino)-cyclopentylsulfanyl]-acetyl}-mutilin in the form of a sodium salt is prepared from 14-O-{[3-(formyl-hydroxy-amino)-cyclopentylsulfanyl]-acetyl}-mutilin analogously to the method of Example 4 Step B.

$^1$H NMR: (DMSO-$d_6$): 7.93, 7.65 (2bs, 1H, CHO), 6.13 (dd, 1H, $H_{19}$, J=17.7 Hz, J=11.2 Hz), 5.55 (d, 1H, $H_{14}$, J=8.1 Hz), 5.06 (dd, 1H, $H_{20cis}$, J=17.7 Hz, J=1.6 Hz), 5.03 (dd, 1H, $H_{20trans}$, J=11.2 Hz, J=1.6 Hz), 4.45 (bs, 1H, 11-OH), 4.14, 3.98 (2bm, 1H, $H_{3'}$), 3.00-3.50 (m, 4H, $H_{11}$, $H_{22}$, $H_{1'}$), 2.4 (s, 1H, H4), 1.35 (s, 3H, $(CH_3)_{15}$), 1.05 (s, 3H, $(CH_3)_{18}$), 0.81 (d, 3H, $(CH_3)_{17}$, J=7.0 Hz), 0.63 (d, 3H, $(CH_3)_{16}$, J=6.7 Hz).

MS-ESI: 520 (M$^-$), 544 (MNa$^+$)

EXAMPLE 7

14-O-{[(1R,3S)-3-(Acetyl-acetoxy-amino)-cyclohexylsulfanyl]-acetyl}-mutilin

14-O-{[(1S,3R)-3-(Acetyl-acetoxy-amino)-cyclohexylsulfanyl]-acetyl}-mutilin 0.36 ml of acetic acid anhydride is added to 500 mg of a mixture of cis diastereomers 14-O-{[((1R,3S)-3-hydroxyamino-cyclohexylsulfanyl]-acetyl}-mutilin and 14-O-{[((1S,3R)-3-hydroxyamino-cyclohexylsulfanyl]-acetyl}-mutilin (Example 1 Step A) in 5 ml of dry THF at 0° C. and the mixture obtained is stirred for 72 hours at room temperature. The mixture obtained is distributed between water and EtOAc and the aqueous layer is extracted with EtOAc 3 times. The combined organic layers are washed with brine and water and dried over MgSO$_4$ and the solvent is evaporated (to dryness) and the evaporation residue is subjected to chromatography (cyclohexane/ethyl acetate=1:2+0.5% AcOH).

416 mg of a mixture of cis diastereomers of 14-O-{[(1R,3S)-3-(Acetyl-acetoxy-amino)-cyclohexylsulfanyl]-acetyl}-mutilin and 14-O-{[(1S,3R)-3-(Acetyl-acetoxy-amino)-cyclohexylsulfanyl]-acetyl}-mutilin are obtained.

$^1$H NMR: δ (400 MHz, DMSO-$d_6$)=6.13 (dd, 1H, $H_{19}$, J=11.0 Hz, J=17.4 Hz), 5.54 (d, 1H, $H_{14}$, J=8.2 Hz), 5.00-5.10 (m, 2H, $H_{20}$), 4.49 (d, 1H, 11-OH, J=5.0 Hz), 4.21 (m, 1H, $H_{3'}$), 3.42 (t, 1H, J=5.5 Hz, $H_{11}$), 2.77 (t, 1H, $H_{1'}$, J=11.0 Hz), 2.40 (s, 1H, $H_4$), 2.21 (s, 3H, CH$_3$ of OAc), 1.90 (bs, 3H, CH$_3$ of NAc), 1.35 (s, 3H, $(CH_3)_{15}$), 1.05 (s, 3H, $(CH_3)_{18}$), 0.81 (d, 3H, $(CH_3)_{17}$, J=7.3 Hz), 0.62 (d, 3H, $(CH_3)_{16}$, J=6.9 Hz).

MS-ESI: 614 (MNa$^+$)

EXAMPLE 8

14-O-{[(1R,3S)-3-(Acetoxyamino)-cyclohexylsulfanyl]-acetyl}-mutilin

14-O-{[(1S,3R)-3-(Acetoxyamino)-cyclohexylsulfanyl]-acetyl}-mutilin 0.093 ml of acetic acid anhydride is added to 500 mg of a mixture of cis diastereomers 14-O-{[(1R,3S)-3-hydroxyamino-cyclohexylsulfanyl]-acetyl}-mutilin and 14-O-{[(1S,3R)-3-hydroxyamino-cyclohexylsulfanyl]-acetyl}-mutilin (Example 1 Step A) in 1.5 ml of dry THF at −15° C. and the mixture obtained is stirred for 1 hour at 0° C. The mixture obtained is distributed between water and EtOAc and the aqueous layer is extracted with EtOAc 3 times. The combined organic layers are washed with brine and water and dried over MgSO$_4$ and the solvent is evaporated (to dryness) and the evaporation residue is subjected to chromatography (cyclohexane/ethyl acetate=1:2+0.5% AcOH).

202 mg of a mixture of cis diastereomers of 14-O-{[(1R,3S)-3-(Acetoxyamino)-cyclohexylsulfanyl]-acetyl}-mutilin and 14-O-{[(1S,3R)-3-(-Acetoxyamino)-cyclohexylsulfanyl]acetyl}-mutilin are obtained.

$^1$H NMR: δ (400 MHz, DMSO-$d_6$)=7.65 (d, 1H, NH, J=5.7 Hz), 6.14 (dd, 1H, $H_{19}$, J=6.4 Hz, J=11.2 Hz), 5.55 (d, 1H, $H_{14}$, J=8.2 Hz), 5.00-5.10 (m, 2H, $H_{20}$), 4.48 (d, 1H, 11-OH, J=6.0 Hz), 3.42 (t, 1H, J=6.0 Hz, $H_{11}$), 2.75-2.88 (m, 1H, $H_{3'}$), 2.62-2.75 (m, 1H, $H_{1'}$), 2.40 (s, 1H, $H_4$), 2.00 (s, 3H, CH$_3$ of OAc), 1.35 (s, 3H, $(CH_3)_{15}$), 1.05 (s, 3H, $(CH_3)_{18}$), 0.81 (d, 3H, $(CH_3)_{17}$, J=7.1 Hz), 0.62 (d, 3H, $(CH_3)_{16}$, J=6.6 Hz).

MS-ESI: 572 (MNa$^+$)

EXAMPLE 9

14-O-{[(1R,3S)-3-(Isobutyryloxyamino)-cyclohexylsulfanyl]-acetyl}-mutilin

14-O-{[(1S,3R)-3-(Isobutyryloxyamino)-cyclohexylsulfanyl]-acetyl}-mutilin 0.44 ml of isobutyric acid anhydride is added to 1331 mg of a mixture of cis diastereomers 14-O-{[(1R,3S)-3-hydroxyamino-cyclohexylsulfanyl]-acetyl}-mutilin and 14-O-{[(1S,3R)-3-hydroxyamino-cyclohexylsulfanyl]-acetyl}-mutilin (Example 1 Step A) in 15 ml of dry THF at 0° C. and the mixture obtained is stirred for 2 hours at 0° C. The mixture obtained is distributed between water and EtOAc and the aqueous layer is extracted with EtOAc 3 times. The combined organic layers are washed with brine and water and dried over MgSO$_4$ and the solvent is evaporated (to dryness) and the evaporation residue is subjected to chromatography (cyclohexane/ethyl acetate=1:1).

1054 mg of a mixture of cis diastereomers of 14-O-{[(1R,3S)-3-(Isobutyryloxy-amino)-cyclohexylsulfanyl]-acetyl}-mutilin and 14-O-{[(1S,3R)-3-(Isobutyryloxy-amino)-cyclohexylsulfanyl]-acetyl}-mutilin are obtained.

$^1$H NMR: δ (400 MHz, DMSO-$d_6$)=7.67 (d, 1H, NH, J=5.5 Hz), 6.13 (dd, 1H, $H_{19}$, J=11.0 Hz, J=17.9 Hz), 5.55 (d, 1H, $H_{14}$, J=6.4 Hz), 5.00-5.10 (n1, 2H, $H_{20}$), 4.50 (d, 1H, 11-OH, J=6.0 Hz), 3.42 (t, 1H, J=6.0 Hz, $H_{11}$), 2.77-2.87 (m, 1H, $H_{3'}$), 2.65-2.74 (m, 1H, $H_{1'}$), 2.52-2.59 (m, 1H, C$\underline{H}$(CH3)$_2$ of $^i$Bu), 2.40 (s, 1H, $H_4$), 1.35 (s, 3H, $(CH_3)_{15}$), 1.08 (d, 6H, $(CH_3)_2$ of $^i$Bu, J=6.9 Hz), 1.05 (s, 3H, $(CH_3)_{18}$), 0.81 (d, 3H, $(CH_3)_{17}$, J=6.9 Hz), 0.63 (d, 3H, $(CH_3)_{16}$, J=6.9 Hz).

MS-ESI: 600 (MNa$^+$)

EXAMPLE 10

14-O-{[(1R,3S)-3-(Pivaloyloxyamino)-cyclohexylsulfanyl]-acetyl}-mutilin
14-O-{[(1S,3R)-3-(Pivaloyloxyamino)-cyclohexylsulfanyl]-acetyl}-mutilin 0.2 ml of pivalic acid anhydride is added to 500 mg of a mixture of cis diastereomers 14-O-{[(1R,3S)-3-hydroxyamino-cyclohexylsulfanyl]-acetyl}-mutilin and 14-O-{[(1S,3R)-3-hydroxyamino-cyclohexylsulfanyl]-acetyl}-mutilin (Example 1 Step A) in 1.5 ml of dry THF at 0° C. and the mixture obtained is stirred for 1.5 hours at 0° C. The mixture obtained is distributed between water and EtOAc and the aqueous layer is extracted with EtOAc 3 times. The combined organic layers are washed with brine and water and dried over $MgSO_4$ and the solvent is evaporated (to dryness) and the evaporation residue is subjected to chromatography (cyclohexane/ethyl acetate=1:1+0.5% acetic acid).

591 mg of a mixture of cis diastereomers of 14-O-{[(1R,3S)-3-(Pivaloyloxy-amino)-cyclohexylsulfanyl]-acetyl}-mutilin and 14-O-{[(1S,3R)-3-(Pivaloyloxy-amino)-cyclohexylsulfanyl]-acetyl}-mutilin are obtained.

$^1$H NMR: δ (400 MHz, DMSO-$d_6$)=7.70 (dd, 1H, NH, J=2.20 Hz, J=5.90 Hz), 6.15 (dd, 1H, $H_{19}$, J=11.0 Hz, J=17.6 Hz), 5.56 (d, 1H, $H_{14}$, J=8.0 Hz), 5.02-5.10 (m, 2H, $H_{20}$), 4.50 (d, 1H, 11-OH, J=5.9 Hz), 3.42 (t, 1H, J=5.9 Hz, $H_{11}$), 2.64-2.88 (m, 2H, $H_{1'}$, $H_{3'}$), 2.40 (s, 1H, $H_4$), 1.35 (s, 3H, $(CH_3)_{15}$), 1.15 (s, 9H, $(CH_3)_2$ of t-Bu), 1.05 (s, 3H, $(CH_3)_{18}$), 0.81 (d, 3H, $(CH_3)_{17}$, J=7.0 Hz), 0.62 (d, 3H, $(CH_3)_{16}$, J=7.0 Hz).

MS-ESI: 614 (MNa$^+$)

The invention claimed is:

1. A compound of general formula I

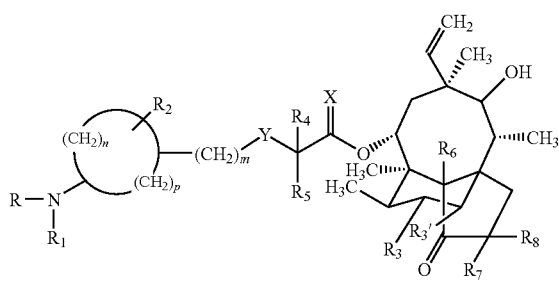

I wherein
R is hydrogen and $R_1$ is hydroxy or acyloxy, or
R is acyl and $R_1$ is hydroxy or acyloxy,
X is sulphur, oxygen or $NR_{10}$, wherein $R_{10}$ is hydrogen or $(C_{1-4})$alkyl;
Y is sulphur or oxygen;
$R_2$ is hydrogen or one or more substituents;
$R_4$ is hydrogen or $(C_{1-4})$alkyl;
$R_5$ is hydrogen or $(C_{1-4})$alkyl;
$R_3$ and $R_3'$ are hydrogen, deuterium, or halogen;
$R_6$, $R_7$ and $R_8$ are hydrogen, halogen or deuterium;
m is a number selected from 0 to 4,
n is a number selected from 0 to 10, and
p is a number selected from 0 to 10;
with the proviso that n plus p are at least 1.

2. The compound according to claim 1, wherein
$R_2$, $R_3$, $R_3'$, $R_4$, $R_5$, $R_6$ and $R_7$ are hydrogen,
X is oxygen,
Y is sulphur,
m is a number selected from 0 to 4, preferably m is 0,
n is a number selected from 0 to 8, preferably from 0 to 7, and
p is a number selected from 0 to 8, preferably from 0 to 7, with the proviso that n plus p are at least 2, preferably less than 9, and more preferably n plus p is 3 or 4.

3. The compound according to claim 1, which is selected from the group consisting of
14-O-[((Hydroxy or acyloxy-amino)-cycloalkylsulfanyl- or -cycloalkyl-oxy)-acetyl, -thioacetyl or -imino-oxy]-mutilins,
14-O-[((Acyl-hydroxy or acyl-acyloxy-amino)-cycloalkylsulfanyl- or -cycloalkyl-oxy)-acetyl, -thioacetyl or -imino-oxy]-mutilins,
14-O-[((Hydroxy or acyloxy-amino-cycloalkyl)-alkylsulfanyl- or alkyl-oxy)-acetyl, -thioacetyl or -imino-oxy]-mutilins,
14-O-[(((Acyl-hydroxy or acyl-acyloxy-amino)-cycloalkyl)-alkylsulfanyl- or alkyl-oxy)-acetyl, -thioacetyl or -imino-oxy]-mutilins,
14-O-[((Hydroxy or acyloxy-amino-cycloalkyloxy)-alkylsulfanyl or alkyl-oxy)-acetyl, -thioacetyl or -imino-oxy]-mutilins, and
14-O-[(((Acyl-hydroxy or acyl-acyloxy-amino)-cycloalkyloxy)-alkylsulfanyl or alkyl-oxy)-acetyl, -thioacetyl or -imino-oxy]-mutilins.

4. The compound according to claim 1, which is selected from the group consisting of [(Hydroxy or acyloxy-amino)-cycloalkylsulfanyl]acetic acid mutilin-14-yl ester and [(Acyl-hydroxy or acyl-acyloxy-amino)-cycloalkylsulfanyl]-acetic acid mutilin-14-yl ester.

5. The compound according to claim 1, which is selected from the group consisting of
[3-(Hydroxyamino)-cyclopentylsulfanyl]acetic acid mutilin-14-yl ester,
[3-(Hydroxyamino)-cyclohexylsulfanyl]acetic acid mutilin-14-yl ester,
[3-(Formyl-hydroxy-amino)-cyclopentylsulfanyl]acetic acid mutilin-14-yl ester,
[3-(Formyl-hydroxy-amino)-cyclohexylsulfanyl]acetic acid mutilin-14-yl ester,
[3-(Acetyl-acetoxy-amino)-cyclohexylsulfanyl]acetic acid mutilin-14-yl ester,
[3-(Acetoxyamino)-cyclohexylsulfanyl]acetic acid mutilin-14-yl ester,
[3-(Isobutyryloxyamino)-cyclohexylsulfanyl]acetic acid mutilin-14-yl ester, and
[3-(Pivaloyloxyamino)-cyclohexylsulfanyl]acetic acid mutilin-14-yl ester.

6. The compound according to claim 1, in the form of a salt.

7. The compound according to claim 1, for use as a pharmaceutical.

8. A method of treatment of bacterial diseases which comprises administering to a subject in need of such treatment an effective amount of a compound of claim 1.

9. A pharmaceutical composition comprising a compound of claim 1, in association with at least one pharmaceutical excipient.

10. A pharmaceutical composition according to claim 9, further comprising another pharmaceutically active agent.

* * * * *